United States Patent [19]

Esmon et al.

[11] Patent Number: 5,120,537
[45] Date of Patent: Jun. 9, 1992

[54] FACTOR XA BASED ANTICOAGULANT COMPOSITIONS

[75] Inventors: Charles T. Esmon; Fletcher B. Taylor, Jr., both of Oklahoma City, Okla.

[73] Assignee: Oklahoma Medical Research Foundation, Oklahoma City, Okla.

[21] Appl. No.: 367,544

[22] Filed: Jun. 14, 1989

[51] Int. Cl.$^5$ ............... A61K 37/547; A61K 37/02; C12N 15/01; C07K 13/00
[52] U.S. Cl. ............... 424/94.64; 435/69.6; 435/212; 435/226; 530/381; 514/2; 514/12; 514/21
[58] Field of Search ............ 424/94.64, 101; 530/381; 435/69.6, 212, 226

[56] References Cited

U.S. PATENT DOCUMENTS 4,775,624 10/1988 Bang et al. ............... 435/226
4,832,849 5/1989 Cardin ............... 424/94.63

FOREIGN PATENT DOCUMENTS 195592 9/1986 European Pat. Off. ........... 435/69.6

OTHER PUBLICATIONS

Leytus et al., Biochemistry, vol. 25, No. 18, 1986, pp. 5098-5102.
Nesheim et al., J. Biol. Chem., vol. 256, No. 13, 1981, pp. 6537-6540.
Lollar et al., Arch. Biochem. Biophys., vol. 233, No. 2, 1984, pp. 438-446.
Leytus et al., PNAS U.S.A., vol. 81, 1984, pp. 3699-3702.
Husten et al., J. Biol. Chem., vol. 262, No. 27, 1987, pp. 12953-12961.
Taylor et al., Thrombosis Research 36, 177-185 (1984).
Taylor et al., J. Clin. Invest. 79, 918-925 (1987).
Nawroth and Stern, Biol. Abstr. 81(11): AB-131 of J. Exp. Med. 163(3): 740-745 (1986).
Esmon et al., "Anticoagulation Proteins C and S", The New Dimensions of Warfarin Prophylaxis ed. Wessler, Becker, and Nemerson, pp. 47-54 (Plenum Press, NY 1987).
Mann, Progress in Hemostasis and Thrombosis, pp. 1-23 (Grune & Stratton 1984).
Hanson and Harker, Proc. Natl. Acad. Sci. USA 85, 3184-3188 (May 1988).
Kaufmann et al., J. Biol. Chem. 261(21), 9622-9628 (1986).
Skogen et al., J. Biol. Chem. 259(4), 2306-2310 (1984).
Jorgensen, M. J., et al., J. Biol. Chem. 262(14), 6729-6734 (1987).
Ehrlich, H. J., et al., J. Biol. Chem. 264(24), 14298-14304 (1989).
Lin, S. W., et al., J. Biol. Chem. 265(1), 144-150 (1990).

Primary Examiner—Jacqueline Stone
Attorney, Agent, or Firm—Kilpatrick & Cody

[57] ABSTRACT

An anticoagulant composition containing an effective amount of factor Xa having the active serine site inactivated that functions rapidly and effectively in vivo to suppress coagulation. In a preferred embodiment, Factor Xa, a serine esterase that forms a complex with Factor Va, Ca++, and phospholipid to catalyze prothrombin activation, is first inactivated with an active site inhibitor, such as dansyl-glu- gly-arg-chloromethyl ketone, to form inactivated factor Xa. In another embodiment, Factor Xa is expressed from a gene sequence wherein the portion encoding the active serine region is modified. The inactivated protein retains the ability to bind to endogenous factor Va in vivo, and has a half-life of approximately ten hours. Administration of inactive factor Xa to the blood of a patient results in the formation of inactive factor Xa-Va complexes in vivo, thereby inhibiting coagulation.

18 Claims, 3 Drawing Sheets

FIGURE 1

FACTOR XA BASED ANTICOAGULANT COMPOSITIONS

The United States Government has rights in this invention by virtue of National Institutes of Health Research Grant No. R01 HL-29807.

BACKGROUND OF THE INVENTION

The present invention relates to anticoagulant compositions based on coagulant factor Xa and methods for the production and use thereof.

Coagulation is the end result of a complex series of reactions in which the end product of each reaction initiates the next reaction. Following vascular injury, there is a rapid activation of an otherwise largely passive process to produce a response at the site of the injury. There are a variety of modulating events that regulate the process in a positive or negative fashion to maintain vascular integrity while retaining general plasma fluidity. As recently summarized by Kenneth G. Mann, in "Membrane-Bound Complexes in Blood Coagulation", *Progress in Hemostasis and Thrombosis*, edited by T. H. Spaet, pages 1-23 (Grune & Stratton 1984), the extensive network of interdependent protein interactions can be represented as a collection of four reaction complexes:

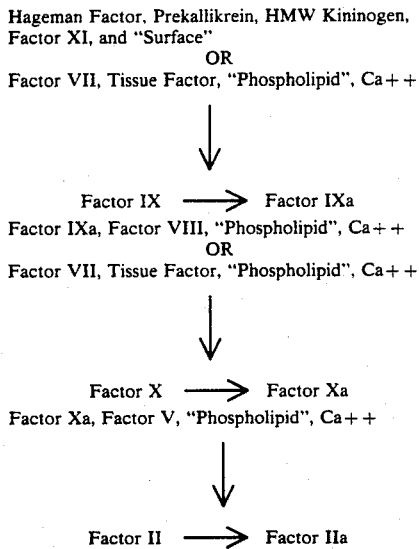

Factor II (prothrombin), Factor X, Factor IX, and Factor VII are vitamin K-dependent proteins which normally circulate as zymogens that are activated to trypsin-like enzymes with active site serine and histidine. In blood, prothrombin is present at about micromolar concentrations; Factor V and Factor X are present at about one-tenth that amount ($10^{-7}$ M). The reaction rate converting Factor II to IIa (thrombin) is about 278,000 fold greater when all components of the complex interact (i.e., Factor II, Factor V, Ca++, and the phospholipid or membrane surface)(Nesheim, et al., *J. Biol. Chem.* 254, 10952-10062 (1979). Deletion of any one component in the complex leads to a drastic reduction in reaction rate.

Although the mechanisms for regulating coagulation and preventing thrombosis ordinarily are remarkably efficient, they can be disrupted by disease, congenital defect or dysfunction, or an inflammatory stimulus which elicits the release of inflammatory mediators such as the monokines tumor necrosis factor (TNF) and interleukin 1 (IL-1).

A wide variety of pathological conditions, including sepsis, especially gram-negative septic shock, beta *Streptococcus* and *Staphylococcus aureus* septicemia, and injuries involving substantial tissue damage, such as burns and crush injuries, can cause the release of inflammatory mediators. Inflammatory mediators are also released in adult respiratory distress syndrome and reperfusion inflammatory syndrome.

In septic shock, the response of the endothelium to the inflammatory stimuli involves both coagulopathy and abnormal permeability. The stimulus activates circulating monocytes and the fixed tissue macrophages in the liver and the lungs. After a lag period of about two to four hours, these blood cells release the monokine inflammatory mediators tumor necrosis factor (TNF) and interleukin 1 (IL-1). These inflammatory stimuli lead to the conversion of endothelial cell surfaces from an anti-coagulant to a procoagulant state, causing intravascular coagulation. When this dysfunction is systemic, it is referred to as disseminated intravascular coagulopathy (DIC). In DIC, the endothelial cell loses its ability to selectively control porosity. The endothelial cells swell and fluid begins leaking into the surrounding tissues, causing anoxia and parenchymal damage. This is accompanied by increased peripheral resistance, decreased venous return and, in many instances, death due to shock.

Septic shock can be simulated in a clinical model by infusion of a lethal dose of *Escherichia coli* in a baboon, F. B. Taylor, "Baboon model of *E. coli* Septic shock staging and observations on the role of the vascular endothelium", chapter 13 *Critical Care State of the Art*, B. F. Fuhrman and W. C. Schoemaker, editors volume 10 (Soc. Critical Care Medicine 1989). The clinical course is characterized as a four stage process. Stage I begins with the inflammatory stimulus, for example, a lethal infusion of *Escherichia coli*, and continues for about 120 minutes. In this stage, the scavenger cells (monocytes and macrophages) and PMNLs are activated and the inflammatory mediators (TNF, IL-1, free hydroxyl radicals, elastase and others) are released. Stage II begins next and continues for about four hours, or from two to six hours after the insult. During this stage, the mediators cause the endothelial cells to become inflamed or perturbed, converting them from an anticoagulant to a procoagulant state. Fibrinogen levels fall and fibrin degradation products increase. The fibrinolytic activity of whole blood increases markedly by one or two hours and then decreases almost immediately at three hours after the insult. Stage III occurs at about six hours following the insult and continues for about four hours. In this stage, the endothelial lose their ability to selectively control permeability and fluid begins to leak into the tissues injuring target organs. In the fourth and final stage, the parenchymal edema produces shunting, peripheral and eventually central anoxia, and decreased mean systemic arterial pressure. Death occurs typically about 24 to 32 hours after the insult.

Treatment for these disorders involving inflammatory mediators usually involves the administration of anticoagulants. Anticoagulants are also used in the prevention of reocclusion following angioplasty, acute organ rejection, and deep vein thrombosis following surgery, and in the treatment of unstable angina, mural thrombosis, stroke, myocardial infarction, and pulmonary embolism.

There are currently a number of known and medically accepted anticoagulant agents. Heparin and vitamin K antagonists such as Coumarin and aspirin are the most widely used anticoagulants. Heparin works in conjunction with another plasma protein, antithrombin III, to inhibit coagulation. Heparin treatment is not effective in all cases since antithrombin III is often at low levels in severe shock and other consumptive coagulation processes. In addition, patients may have adverse reactions to heparin, including heparin induced thrombocytopenia. Further, maintenance of an effective heparin dose in vivo has proven difficult.

Coumarin drugs are slow to be effective, taking several days before antithrombotic effects are observed. Bleeding is a common complication of vitamin K antagonist treatment and, as with heparin, the effective dose is hard to monitor since the required dose is impacted by both diet and other drugs that are present in the patient especially antibiotics. In addition, there is a rare complication that leads to skin necrosis and potential loss of limbs or, in exceptional cases, the individual's life (Esmon, C. T., et al., "Anticoagulant Proteins C and S". in *New Dimensions of Warfarin Prophylaxis*. Wessler, et al., eds., Plemum Publishing Corp., New York, 47–54, 1987). Aspirin is limited to inhibition of platelet aggregation and is of little efficacy in treating patients at severe risk of thrombosis.

An alternative method for the suppression of clotting which has been proposed is the direct administration of compounds which inhibit thrombin. Many studies have been done wherein the active site of the coagulation enzymes is inhibited in vitro using a variety of different types of inhibitors, especially low molecular weight serine esterase inhibitors such as diisopropylfluorophosphate (DFP) or phenylmethanesulfonyl fluoride (PMSF). For example, Skogen, et al., in *J. Biol. Chem.* 259(4), 2306–2310 (1984), used the serine esterase inhibitor (p-amidinophenyl)methanesulfonyl fluoride (pPMSF) to inhibit the active site of factor Xa, both in its native form and in modified form, to determine the role of factor Va binding to factor Xa in formation of the prothrombinase complex.

Hanson, et al., *Proc. Natl. Acad. Sci. USA*, 85:3184–3188, (1988), used a synthetic antithrombin, D-phenylalanyl-L-prolyl-L-arginyl chloromethyl ketone, PPACK, to block arterial thrombosis by specific interaction with thrombin. A disadvantage to this approach, however, is the requirement for administration of high levels of reactive compounds having unknown potential side effects. Further these small compounds are cleared rapidly form the blood stream and the monitoring of a maintenance dose is complex.

There are many problems in trying to extrapolate from in vitro studies involving inhibition of coagulation factors to in vivo uses of an inhibited protein as an anticoagulant. Modified proteins, such as an inactivated coagulation factor, may be cleared much more rapidly from the blood by cells of the reticuloendothelial system than the unmodified proteins. The coagulation process is complex, involving interactions between proteins in the intrinsic and extrinsic pathways and cell surface receptors. In vitro, the proteins are usually present in purified form and there are generally no cell surface receptors or other plasma protein components present which may alter interactions with the inhibited protein. For example, in vivo studies using thrombin with the active site inactivated demonstrated that infusion of this proteolytically inactive protein actually induced a procoagulant state, possibly because of binding with endogenous inhibitors of coagulation, such as thrombomodulin.

A rapid and effective anticoagulant having a relatively long half-life in vivo and free from the side effects and shortcomings of the ones presently in use would have utility in the prevention of reocclusion following angioplasty, acute organ rejection, and deep vein thrombosis following surgery, and in the treatment of unstable angina, mural thrombosis, stroke, myocardial infarction, and pulmonary embolism.

It is therefore an object of the present invention to provide a safe, effective, and fast acting anticoagulant composition for use in vivo.

It is a further object of the present invention to provide a method for the production of anticoagulant compositions for in vivo application.

It is a still further object of the present invention to provide a method of treating individuals in need of such treatment with an effective amount of an anticoagulant composition.

SUMMARY OF THE INVENTION

An anticoagulant composition containing an effective amount of factor Xa having the active serine site inactivated that functions rapidly and effectively in vivo to suppress coagulation. In a preferred embodiment, factor Xa, a serine esterase that forms a complex with factor Va, Ca++, and phospholipid to catalyze prothrombin activation, is first inactivated with an active site inhibitor, such as dansyl-glu-gly-arg-chloromethyl ketone, to form inactivated factor Xa (fXa$_i$). In another embodiment, Factor Xa is expressed from a gene sequence wherein the portion encoding the active serine region is modified. The inactivated protein retains the ability to bind to endogenous factor Va in vivo. Administration of inactive factor Xa to the blood of a patient results in the formation of inactive factor Xa-Va complexes in vivo, thereby inhibiting coagulation.

In the preferred method for inhibiting coagulation, an amount of inactivated factor Xa effective to inhibit coagulation by binding to free factor Va, in combination with a pharmaceutically acceptable carrier, is administered to a patient. In some cases, as in the case of septic shock where inactivated factor Xa alone is not efficacious in treating the permeability disorders it may be desirable to combine the inactivated factor Xa with other compounds, such as antibodies to tumor necrosis factor (TNF), antithrombin III (ATIII), and activated protein C, a naturally occurring anticoagulant. Surprisingly, as shown by studies conducted in a primate septic shock model, the modified factor Xa has a half-life in vivo of approximately ten hours, so that the anticoagulant must be administered only once or twice a day to inhibit clotting.

BRIEF DESCRIPTION OF THE DRAWINGS

FIG. 1 is the amino acid sequence for factor X, adapted from Leytus, et al., *Biochemistry* 25, 5101 (1986), showing the active site serine 185 and cleavage site to activate factor X into factor Xa.

DETAILED DESCRIPTION OF THE INVENTION

Figure 2A:
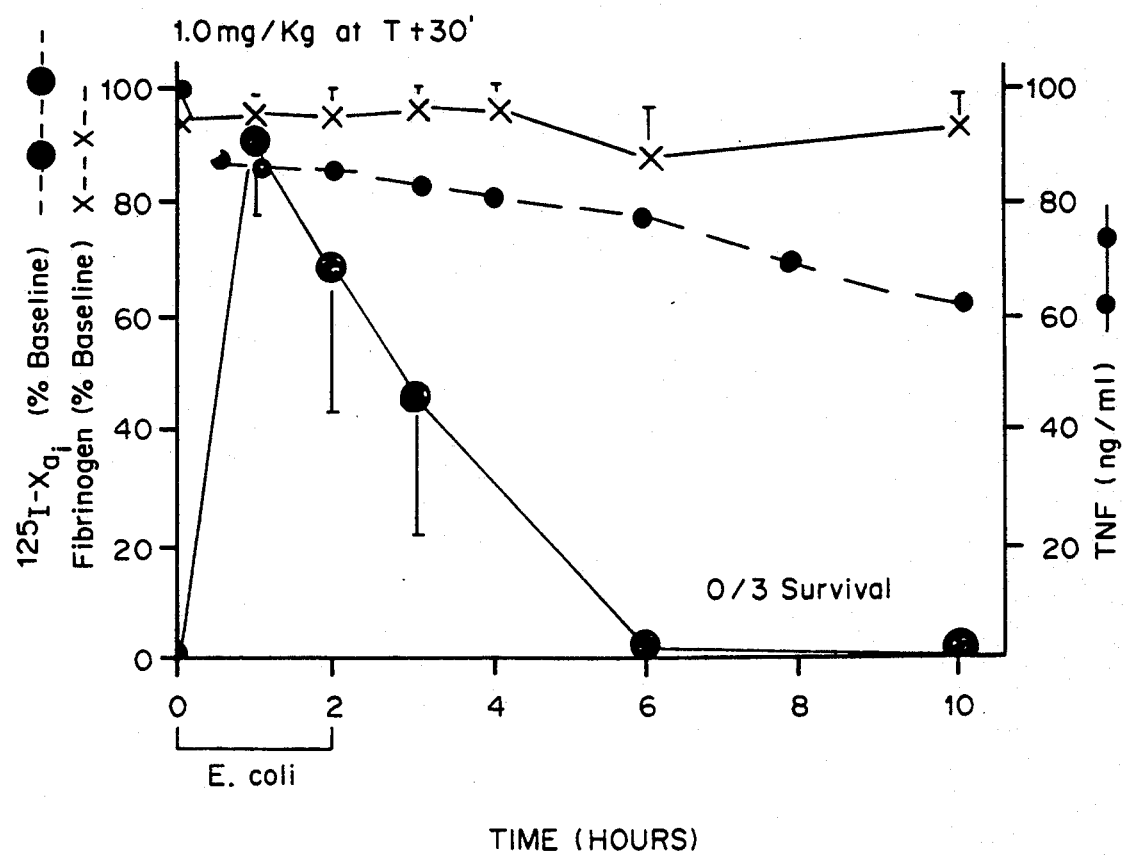
FIGS. 2A and 2B are graphs comparing the effect of inactivated factor Xa (FIG. 2A) versus untreated controls (FIG. 2B) in baboons in response to administration of lethal dosages of *E. coli*, showing the rate of clearing of administered inactive factor Xa (-●--●-), percent level of fibrinogen relative to baseline level (-X--X-), and level of tumor necrosis factor (TNF) (-●--●-) as a function of time (hours).

It has now been demonstrated that inactivated factor Xa can act as a rapid, effective anticoagulant in vivo by complexing endogenous factor Va. The exogenously administered inactivated factor Xa competes for and diminishes the free factor Va available to complex with endogenous factor Xa. The reduction of the available factor Va pool effectively inhibits the coagulation process.

Anticoagulants having in vivo half-lives of at least five minutes, and preferably greater than one hour, are most desirable. As demonstrated in the baboon septic shock model, the in vivo half-life of the modified inactivated factor Xa is approximately ten hours. The normal in vivo half life of factor X is on the order of ten hours. In contrast, the normal in vivo half-life of factor Xa is only about thirty seconds. The significantly greater half-life of the modified inactivated factor Xa greatly increases its utility as an anticoagulant since it can be administered to a patient once or twice daily with efficacy, rather than in much more frequent intervals.

Figure 1:
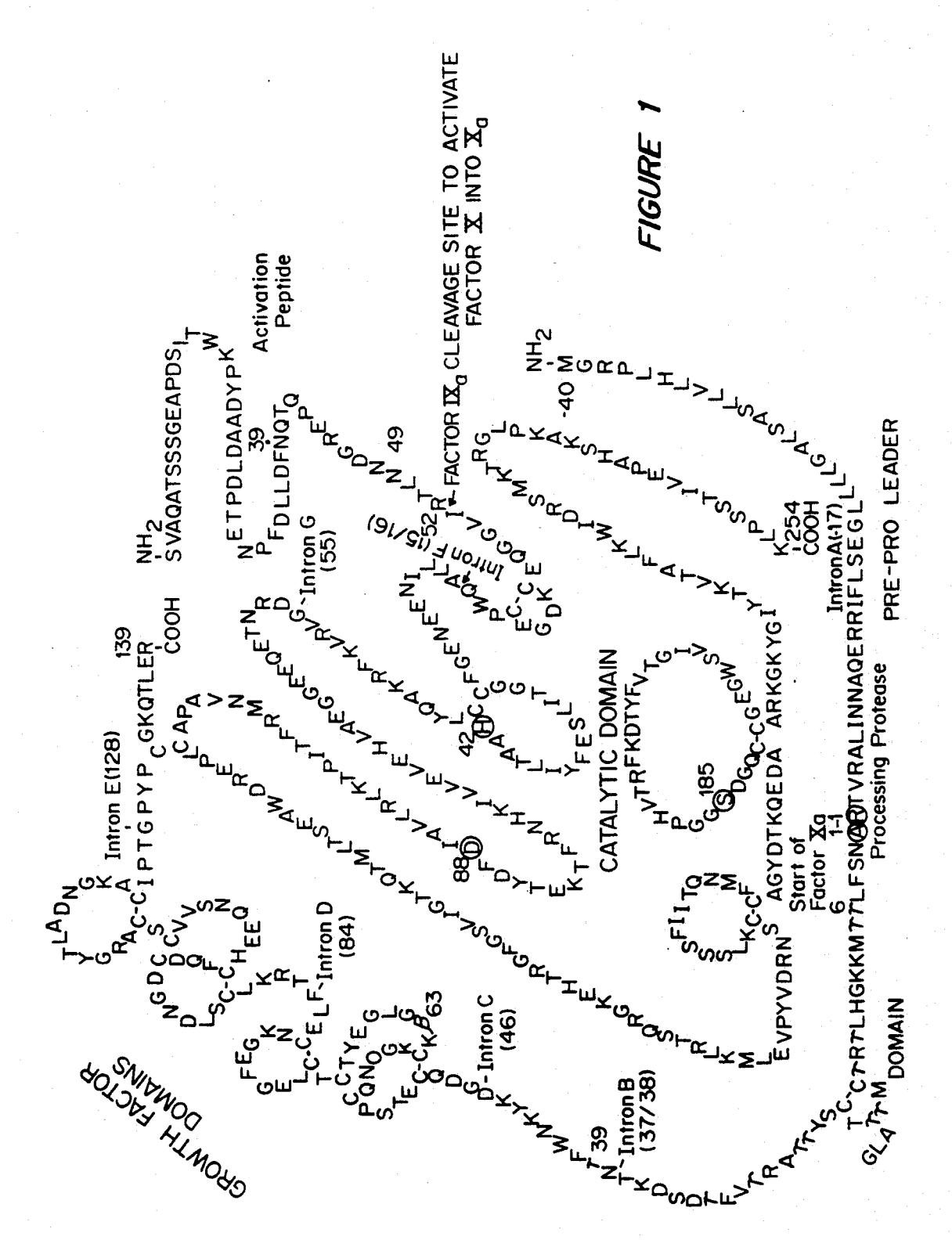

A suitable factor Xa composition for administration to a patient is prepared either by inactivation of factor Xa using a serine esterase inhibitor or the Fab portion of an antibody to the active serine region of the factor Xa (Asp-His-Ser), or by modification of the protein to delete or inactivate the active serine region. The sequence of factor Xa has been known for a number of years and the gene cloned, as described by Leytus, et al., in *Biochemistry* 25, 5098-5102 (1986), as shown in FIG. 1. Since the proteolytically active region is known, one skilled in the art can delete the nucleotide sequences encoding this region of the protein, to express a polypeptide having factor Xa activity that is protelytically inactive and therefore unable to activate prothrombin to thrombin, using recombinant methodologies such as those employed by Leytus, et al., in Biochemistry 25, 5098-5102 (1986), in isolating and characterizing the gene sequence for factor X or methods similar to those employed for expression of factor IX, as described by Kaufman, et al., "Expression, purification, and Characterization of Recombinant gamma-Carboxylated Factor IX synthesized in Chinese Hamster Ovary Cells", *J. Biol. Chem.* 261:9622-9628, 1986).

This methodology is summarized in part as follows.

Oligonucleotide sequences homologous to Factor X are synthesized and labeled for use as hybridization probes. The resultant probes are used to screen a cDNA library, such as the lambda Charon 4A library of Lawn, et al., *Cell* 1157-1174 (1978) and lambda EMBL3 library of Yoshitake, et al., *Biochemistry* 24, 3736-3750 (1985), using plaque hybridization, as described by Benton & Davis, *Science* 196, 180-182 (1977) and Woo *Methods Enzymol.* 68, 389-395 (1979). Genomic DNA inserts are released from purified recombinant phage DNA by restriction enzyme digestion and subcloned into a plasmid vector such as pUC, using the method of Vieira & Messing, Gene 19, 259-268 (1982) Plasmid DNA is prepared by the modified method of Micard, et al., *Anal. Biochem.* 148, 121-126 (1985) of the alkaline extraction procedure of Birnboim & Doly, *Nucleic Acids Res.* 7, 1513-1523 (1979). Genomic DNA inserts are mapped by single and double restriction enzyme digestion followed by agarose gel electrophoresis, Southern blotting (Southern, *J. Mol. Biol.* 98,503-517 (1975)) and hybridization to radio-labeled cDNA probes prepared by nick translation (Rigby, et al., *J. Mol. Biol.* 113, 237-251 (1977)) of DNA fragments isolated from agarose gels. Selected fragments from restriction enzyme digests of recombinant plasmids are subcloned into M13 bacteriophage vectors using the procedure of Messing, *Methods Enzymol.* 101, 20-78 (1983). Genomic subclones in M13 vectors that hybridize to cDNA probes for factor X are then isolated and sequenced by the dideoxy chain termination method of Sanger, et al., *Proc. Natl. Acad. Sci. U.S.A.* 74, 5463-5467 (1977), using synthetic oligonucleotide primers. The gene sequences are then expressed under the control of an appropriate promoter in either a bacterial or eukaryotic host.

The presence of factor X can be determined by clotting assays, immunochemical assays using anti-factor X antibodies, or a solid-phase enzyme-linked immunosorbent assay system.

For example, factor X coagulant activity can be determined with a two-stage assay using Factor X-deficient plasma. One unit of Factor X activity represents the amount of Factor X in 1 ml of normal human pooled plasma. The clotting assay reflects the rate of thrombin production. Solutions of factor Xa are incubated in the presence or absence of the other components of the prothrombinase complex without prothrombin. The reaction is brought to volume with 0.1 M NaCl, 0.02 M Tris-HCl, pH 7.6. After equilibration for 5 min prothrombin is added and a stopwatch started. At various time points, aliquots are added to clotting tubes containing fibrogen (2.5 mg/ml final concentration). The clotting time is recorded, and the units of thrombin calculated from standard curves generated from purified thrombin with a specific activity of 1200 units/absorbance unit at 280 nm. The rate of thrombin formation is then calculated for each incubation and expressed as moles of thrombin formed per min/mol of factor Xa. In reactions where higher amounts of thrombin are formed, the samples are diluted into 0.1 M NaCl, 0.02 M Tris-HCl, 1 mg/;ml of bovine serum albumin, pH 7.5, before addition to the fibrinogen.

The sequence for factor X is shown in FIG. 1. General methods for site directed mutagenesis are known which can be used to modify the region of the gene encoding the active serine to yield a proteolytically inactive factor Xa. Site directed mutagenesis is defined as altering the nucleotide sequence of a gene at a specific site in a defined way. Generally, a short oligonucleotide (20-30 bases of DNA) which contains the desired mutation is synthesized and hybridized to the complementary template containing the wild-type DNA sequence. The short oligo is then extended using T4-DNA polymerase in the presence of exogenously added deoxy ribonucleotide triphosphates (dATP, dGTP, dCTP and dTTP). The resulting product is a heteroduplex molecule which contains a mismatch representing the desire mutation in one strand of the DNA duplex. This product is then introduced into a bacteria (usually *E. coli*) by transformation. The mutation is fixed in the bacteria as the result of replication. Both wild-type and mutant duplex DNA is produced in bacteria following replication. The bacterial colonies harboring the mutant DNA molecules are identified, cultured and the desired DNA molecules are extracted. After confirming the mutation by DNA sequencing, the mutant gene is then subcloned into an expression vector and transfected into an appropriate cell line to produce the mutant protein.

The inactivated factor Xa can be prepared from factor X isolated from plasma of the same or different species as the subject to be treated. For example, the polypeptides useful in the anticoagulant compositions can be obtained from equine, bovine, porcine, sheep goat, human, or monkey blood. Effectiveness between species has been demonstrated in several species, for example, human and bovine. Long term administration of cross-species administration of inactivated factor Xa should be avoided, however, since there exists the potential for an immune reaction. Alternatively, factor X, or polypeptides having factor X activity that can be activated to possess factor Xa activity using a factor X activating enzyme from Russell's viper venom, factor IXa in combination with phospholipid and Ca++, or factor VIIa, tissue factor and Ca++, can be expressed from the cloned gene for factor X.

For example, factor X can be isolated from plasma using the method of Owen, et al., *J. Biol. Chem.* 249, 594-605 (1974). Trace contaminants are removed by chromatography of the redissolved ammonium sulfate (15-55% saturation) precipitate on an Ultragel 44 TM column (1.5×100 cm) equilibrated in 0.1 M NaCl, 0.02 M Tris-HCl, 5 mM benzamidine/HCl, pH 7.5. Fractions containing factor X activity are pooled and applied to a m-aminobenzamidine-Sepharose TM column (2×20 cm) equilibrated in the same buffer. Factor X is eluted from the column with 2.0 M NaCl, 0.02 M Tris-HCl, 0.02 M benzamidine/HCl, pH 7.5. Fractions containing factor X activity are pooled and dialyzed against 0.1 M NaCl, 0.02 M Tris-HCl, pH 7.5. Factor X is assayed by the method of Bachman, et al., *Thromb. Diath. Haemmorrh.* 2, 24-38 (1958). Factor X can be activated to factor Xa with the X coagulant protein purified from Russell's viper venom, described by C. T. Esmon, Ph.D. dissertation, Washington University (1973), and assayed as described by Bajaj and Mann, *J. Biol. Chem.* 248, 7729-7741 (1973). The factor Xa is further purified on QAE-Sephadex.

Monoclonal autibodies are produced as follows.

BALB/c mice are injected peritoneally with 50-100 μg of purified protein antigen in complete Freund's adjuvant. The mice are again immunized after 3 weeks with protein antigen emulsified in incomplete Freund's adjuvant and after 6 weeks with protein antigen in TBS (0.1 M NaCl 0.02 M Tris-HCl pH 7.5). Four days later, spleen cells are fused with a mouse myeloma cell line, such as PX63AG8-653, using 35% polyethylene glycol 1450, according to standard techniques, as described by Laurell, M., K. Ikeda, S. Lindgren, J. Stenflo, FEBS Letters 191, 75-81 (1985); Wakabayashi, K., Y. Sakata, N. Aoki, *J. Biol. Chem.* 261, 11097-11105 (1986); Borrebaeck, C.A.K., M. E. Etzler, *J. Biol. Chem.* 256, 4723-4725 (1981); Kohler, G., C. Milstein, Nature 256, 495-497 (1975).

Cells are grown in HAT medium to select for hybridomas. After four weeks, supernatants from fused cells are screened for antigen-specific antibody production by solid-phase enzyme-linked immunoadsorbent assay ELISA) in the presence and absence of 5 mM $Ca^{2+}$. Culture supernatants are diluted 1:4 into buffer containing either 5 mM $CaCl_2$ or 5 mM EDTA for assay. All reagents (antigen, wash buffers, detection antibodies) contain the appropriate calcium or EDTA concentrations.

Clones of interest, based on positive ELISA results, are then recloned at least two times by limiting dilution onto murine peritoneal lavage feeder cells. For production of ascites fluid, BALB/c mice are initially primed with pristane and 14 days later injected peritoneally with 0.1 ml of 10 mg/ml cyclophosphamide to immunocompromise the animal. Twenty-four hours later, $3-6 \times 10^6$ cells are injected intraperitoneally. After 7-10 days, ascites fluid is collected.

The monoclonal antibodies are purified from ascites fluid by $NH_4SO_4$ fractionation (ascites fluid is diluted 1:1 with water, then precipitated by addition of equal volumes of saturated $NH_4SO_4$), followed by chromatography on QAE-Sephadex Q-50 (the ammonium sulfate precipitate is collected by centrifugation, desalted into 0.027 M Tris $PO_4$, pH 6.3, chromatographed on column at a ratio of 1 ml resin/ml ascites, equilibrated in 0.027 M Tris $PO_4$, pH 6.3, developed with a five times column volume linear gradient of 0 to 0.4 M NaCl over approximately eight hours), followed by precipitation of the partially purified antibody with 50% $NH_4SO_4$ and Sephadex G200 column chromatography in 0.1 M NaCl 1 mM MOPS, pH 7.5.

Fab fragments of IgG are prepared by 2 h digestion of the antibody at 37° C. with immobilized papain (Pierce). The resulting Fab fragments were purified to homogeneity by absorption against immobilized staph protein A and gel permeation chromatograph (Sephadex G150; Pharmacia).

It is essential that the modified or inhibited factor Xa retain the factor Va binding activity. Factor Xa normally interacts in approximately a one to one molar ratio with factor Va. It is preferable if it also retains its ability to bind to phospholipid. It is not known which of the factor Xa sequences have the factor Va binding activity. It has been demonstrated that blockage of the active serine with a serine esterase inhibitor does not interfere with the binding activity. Binding of anthrombin III to factor Xa does interfere with factor Va binding. As used herein, "inactivated factor Xa" refers to either modified or inhibited factor Xa or factor Xa polypeptides having normal binding affinity for factor Va but little or no serine esterase activity.

Factor Xa can be reacted with 5-(dimethylamino)-naphthalenesulfonyl-glutamylglycylarginyl (DEGR) chloromethyl ketone to yield DEGR-Xa, an analogue of factor Xa with a fluorescent dye attached covalently to the active site, to determine availability of the factor Va binding site following inactivation of the active serine site, as described by Husten, et al., *J. Biol. Chem.* 262(27), 12953-12960 (1987). When DEGR-Xa is titrated with phosphatidylcholine/phosphatidylserine vesicles containing octadecylrhodamine, fluorescence energy transfer is observed between the donor dyes in the active sites of the membrane-bound enzymes and the acceptor dyes at the outer surface of the phospholipid bilayer. Based on the dependence of the efficiency of singlet-singlet energy transfer upon the acceptor density and assuming $kz = \frac{2}{3}$, the distance of closest approach between the active site probe and the surface of the phospholipid bilayer averages 61 Angstroms in the absence of factor Va and 69 Angstroms in the presence of factor Va. Association of factor Xa with factor Va on the membrane surface to form the prothrombinase complex results in a substantial movement of the active site of the enzyme relative to the membrane surface.

Inhibitors which covalently bond to the factor Xa are preferred. A polypeptide having factor Xa activity can be inactivated using active site inhibitors known to those skilled in the art. Examples of known active site inhibitors include (p-aminophenyl)methyl sulfonyl fluoride (PMSF), diisopropyl fluorophosphate (DFP), and dansyl-glu-gly-arg-chloromethyl ketone (Dns-Glu-Gly-Arg). The selective, irreversible inhibition of factor Xa using Dns-Glu-Gly-Arg is described by Nesheim, et al., in *J. Biol. Chem.* 256 (13), 6537-6540 (1981) and in the following example.

The anticoagulant treatment methods encompassed by the present invention utilize a pharmaceutical composition containing a polypeptide, characterized by having the ability to bind factor Va while at the same time being unable to act as a protease to activate prothrombin to thrombin, in combination with a pharmaceutically acceptable carrier for administration to the subject to be treated, most preferably a carrier for i.v. administration such as saline, phosphate buffered saline, or a "synthetic plasma". The amount of inactivated factor Xa is determined on the basis of the amount of factor Va to be removed from the coagulation process. In general, factor Xa interacts with factor Va in a one to one ratio. One can calculate the required dosage based on the concentration of factor V in blood and platelets, on the order of $10^{-7}$ M, although most of the factor V is not in the activated state. Accordingly, one would generally administer an amount of inactivated factor Xa which is substantially less than $10^{-7}$ M. In general, the effective amount of the inactivated factor Xa will be in the range of between 1 ng inactivated factor Xa/ml of blood up to 10 micrograms inactivated factor Xa/ml of blood.

The inactivated factor Xa composition can also be used in the prevention of reocclusion following angioplasty, acute organ rejection, and deep vein thrombosis following surgery. Additionally, the anticoagulant compositions may be useful in the treatment of unstable angina, mural thrombosis, stroke, myocardial infarction, and pulmonary embolisms.

In some situations, it may be desirable to combine the inactivated factor Xa with other compounds, particularly when treating septic shock where administration of inactivated factor Xa alone is not effective in preventing death due to alteration in permeability resulting from the infusion of Gram negative bacteria. As disclosed in co-pending application, U.S. Ser. No. 139,922 entitled "Treatment of Dysfunctional Vascular Endothelium Using Activated Protein C", filed Dec. 31, 1987 by Fletcher B. Taylor, Jr. and Charles T. Esmon, activated protein C (APC) can be administered in combination with antibodies to TNF, available from Cetus Corporation, or ATIII.

Except as otherwise noted, the various reagents, coagulation factors and inhibitors are commercially available from companies such as Calbiochem, Sigma Chemical Company, Cetus, and Eli Lilly.

EXAMPLE 1

Effect of Inactivated Factor Xa (factor Xa-i) to lethal septic shock in baboons

Methods

Factor X was isolated and purified from bovine blood as follows. Briefly, bovine blood was collected into oxalate as an anticoagulant, the cells were removed by centrifugation, and the plasma adsorbed onto $BaSO_4$. The partially purified factor X was then eluted with citrate, chromatographed on QAE Sephadex ™, and blue Sepharose ™ to yield the pure protein, as described in detail by E. R. Guinto, in her Ph.D. dissertation, University of Oklahoma Health Sciences Center, Oklahoma City, Ok. (1983).

Purified factor X was then activated with factor X activating enzyme purified from Russell's viper venom, *Vipera russellii*, prepared as described by Esmon CT, Ph.D., dissertation, Washington University, St. Louis, Mo. (1973) to produce factor Xa. Factor Xa was then isolated by ion exchange chromatography on QAE Sephadex.

Factor Xa at 0.65 mg/ml was subsequently reacted with 1.2 ml of dansyl-glu-gly-arg-chloromethyl ketone (Calbiochem) at 1 mg/ml for 30 min at room temperature to yield inactivated factor Xa (DERG-Xa). Excess inhibitor was removed by exhaustive dialysis in 0.1 M NaCl 0.001 M Tris-HCL, pH 7.5. Although less than 0.1% of the activity remained, the sample (9.2 ml, 0.65 mg/ml) was treated with antithrombin III (0.25 ml, 1.75 mg/ml), to inhibit any residual factor Xa activity.

Bound Human factor Xa which had been inactivated by blocking the active site with DEGR (Xa-i), was dialyzed into 0.02 M Tris, 0.1 M NaCl, pH 7.5. This human Xa-i was radioiodinated using Enzymobeads (Biorad) according to the manufacturer's instructions. Briefly to a 5 ml polystyrene tube, 0.8 ml Xa-i (0.79 mg, 14 $\mu$M), 10 $\mu$l 2.76 M Tris-HCl, pH 7.2, 100 $\mu$l Enzymobeads, 2 $\mu$l $Na^{125}I$ (0.2 mCi) and 100 $\mu$l $\beta$-glucose was added, yielding 14 $\mu$Ci/$\mu$M Xa-i. The tube contents were mixed and it was allowed to stand at room temperature for 18 min. The reaction was stopped by de-salting the solution using a PD-10 column (Pharmacia) equilibrated in 0.02 M Tris, 0.1 M NaCl. The Xa-i solution was added to the column and eluted with 0.02 M Tris, 0.1 M NaCl. 0.5 ml fractions were collected. Aliquots of each fraction were counted in a gamma counter (Nuclear Enterprises NE 1600). The 0.5 ml fraction containing the highest concentration of $^{125}I$ was used in the baboon studies. The Xa-i concentration was 0.79 mg/ml and the $^{125}I$ concentration was 230 CPM/$\mu$l (114,750 CPM total).

Baboons were subjected to infusion of lethal dosages of *E. coli*, as described in U.S. Ser. No. 139,922, entitled "Treatment of Dysfunctional Vascular Endothelium Using Activated Protein C", filed Dec. 31, 1987 by Fletcher B. Taylor, Jr. and Charles T. Esmon. Radioactively labeled DEGR-Xa was infused at a level of 1 mg/kg body weight. The fibrinogen and tumor necrosis factor levels were monitored as a function of time (hours). The level of radioactive DEGR-Xa was also measured.

Results

Figure 2B:
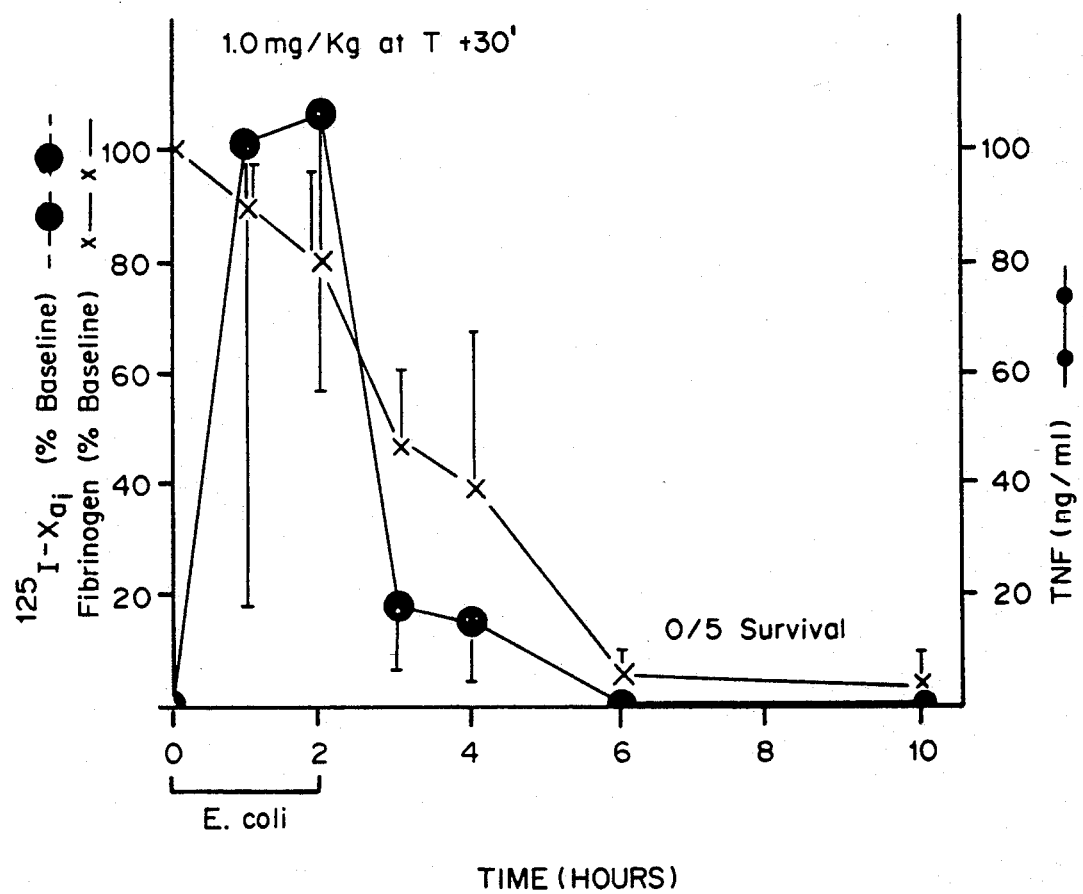

The results are shown in FIGS. 2A and 2B, graphing the % radiolabelled factor Xa, % fibrinogen, ng TNF/ml blood, and survival, over a period of 10 hours.

Eight animals were measured. All eight succumbed to the *E. coli*. However, in animals infused with inactivated factor Xa (fXa-i), the fibrinogen levels remained at greater than 80% over a period of ten hours, versus a 50% decrease by three hours, and almost no detectable fibrinogen by six hours, in control animals.

Very often, modified proteins are rapidly cleared in vivo, thus decreasing their pharmacological utility. However, as seen in FIG. 2A, the DEGR-Xa is cleared from the circulation with a half-life in excess of 10 hours.

Despite the effectiveness of the inactivated factor Xa as an anticoagulant, demonstrated by the maintenance of the fibrinogen levels, the release of TNF was very similar in both control and treated animals and the animals succumbed, possibly as a result of perturbations in permeability.

In summary, the results show that, in a baboon model of Gram negative septic shock, inactivated factor Xa inhibits fibrinogen consumption and is an effective anticoagulant, having a half-life of at least 10 hours. Further, it is apparent that inactivated factor Xa derived from a species other than that of the subject is effective as an anticoagulant.

Modifications and variations of the composition and methods for inhibiting coagulation using inactivated factor Xa will be obvious to one skilled in the art in view of the foregoing description. Such modifications and variations are intended to fall within the scope of the appended claims.

We claim:

1. An anticoagulant composition comprising:
   an anticoagulant consisting essentially of factor Xa, or a polypeptide fragment thereof, having little or no serine esterase activity, which is capable of binding coagulation factor Va in the blood of a mammal, free of unreacted serine esterase inhibitors; and
   a pharmaceutically acceptable carrier, wherein the inactivated factor Xa is in a dosage effectively inhibiting factor Va binding with proteolytically active factor Xa in vivo over a period of greater than five minutes.

2. The anticoagulant of claim 1 wherein the factor Xa is produced by enzymatic cleavage of isolated factor X.

3. The anticoagulant of claim 2 wherein the factor X is isolated from plasma from an animal species selected from the group consisting of equine, bovine, porcine, human, sheep, goat, and non-human primates.

4. The anticoagulant of claim 1 wherein the factor Xa or factor Xa fragment is produced by recombinant engineering.

5. The anticoagulant of claim 1 wherein the factor Xa binds phospholipid.

6. The anticoagulant of claim 1 wherein the active site serine region of said factor Xa or polypeptide fragment thereof, is inactivated with an inhibitor selected from the group consisting of chloromethyl ketones, fluorophosphates, sulfonyl fluoride inhibitors, and antibodies or fragments thereof which interact with the active site of factor Xa without blocking the factor Va binding activity.

7. The anticoagulant of claim 6 wherein the inhibitor is selected from the group consisting of dansyl-glu-gly-arg-chloromethyl ketone, para-amidinophenylmethyl sulfonyl fluoride, and diisopropyl fluorophosphate and all unbound inhibitor is removed from the inactivated factor Xa.

8. The anticoagulant of claim 1 wherein the carrier is selected from the group consisting of water, saline, synthetic plasma, and physiological buffers suitable for intravenous administration.

9. A method for inhibiting coagulation comprising:
   providing to a patient an anticoagulant composition containing an anticoagulant consisting essentially of factor Xa, or a polypeptide fragment thereof, having little or no serine esterase activity, which is capable of binding coagulation factor Va in the patient, free of unreacted serine esterase inhibitors; and a pharmaceutically acceptable carrier, wherein the inactivated factor Xa is in a dosage effecitvely inhibiting coagulation by inhibiting factor Va binding with proteolytically active factor Xa in vivo over a period of greater than five minutes.

10. The method of claim 9 further comprising producing the factor Xa by enzymatic cleavage of isolated factor X.

11. The method of claim 9 wherein the factor X is isolated from plasma from an animal species selected from the group consisting of equine, bovine, porcine, human, sheep, goat, and non-human primates.

12. The method of claim 9 wherein the factor Xa or factor Xa fragment is produced by recombinant engineering.

13. The method of claim 9 wherein the factor Xa phospholipid binding region is not inactivated or removed.

14. The method of claim 9 wherein said active site serine region is inactivated by reaction with an inhibitor selected from the group consisting of chloromethyl ketones, fluorophosphates, sulfonyl fluoride inhibitors, and antibodies or fragments thereof that interact with the active site of factor Xa without blocking the factor Va binding activity, and unreacted inhibitor is removed from the inactivated factor Xa before administration to the patient.

15. The method of claim 14 wherein the inhibitor is selected from the group consisting of dansyl-glu-gly-arg* chloromethyl ketone, para-amidinophenylmethyl sulfonyl fluoride, and diisopropyl fluorophosphate.

16. The method of claim 9 wherein the carrier is selected from the group consisting of water, saline, synthetic plasma, and physiological buffers suitable for intravenous administration.

17. The method of claim 9 wherein the effective amount of the anticoagulant composition is between about 1 ng inactivated factor Xa/ml of blood up to 10 micrograms inactivated factor Xa/ml of blood.

18. The method of claim 9 further comprising administering an effective amount of the anticoagulant composition to a patient to inhibit disseminated intravascular coagulation.

* * * * *